(12) United States Patent
Zhang et al.

(10) Patent No.: US 12,012,611 B2
(45) Date of Patent: Jun. 18, 2024

(54) SERUM-FREE COMPLETE MEDIUM FOR INDUCING DIFFERENTIATION OF A MESENCHYMAL STEM CELL TO A CORNEAL EPITHELIAL CELL

(71) Applicant: QINGDAO RESTORE BIOTECHNOLOGY CO., LTD., Qingdao (CN)

(72) Inventors: Bingqiang Zhang, Shandong (CN); Mengmeng Chen, Shandong (CN); Wei Zou, Qingdao (CN); Xueqi Fu, Qingdao (CN)

(73) Assignee: QINGDAO RESTORE BIOTECHNOLOGY CO., LTD., Qingdao (CN)

( * ) Notice: Subject to any disclaimer, the term of this patent is extended or adjusted under 35 U.S.C. 154(b) by 634 days.

(21) Appl. No.: 17/283,491

(22) PCT Filed: May 25, 2020

(86) PCT No.: PCT/CN2020/092071
§ 371 (c)(1),
(2) Date: Apr. 7, 2021

(87) PCT Pub. No.: WO2021/212592
PCT Pub. Date: Oct. 28, 2021

(65) Prior Publication Data
US 2022/0041982 A1 Feb. 10, 2022

(30) Foreign Application Priority Data
Apr. 20, 2020 (CN) .......................... 202010310198.9

(51) Int. Cl.
*C12N 5/079* (2010.01)
(52) U.S. Cl.
CPC ........ *C12N 5/0621* (2013.01); *C12N 2500/30* (2013.01); *C12N 2501/14* (2013.01); *C12N 2501/235* (2013.01); *C12N 2501/37* (2013.01); *C12N 2506/1346* (2013.01)
(58) Field of Classification Search
CPC .......... C12N 2500/30; C12N 2501/235; C12N 2501/37; C12N 2506/1346
See application file for complete search history.

(56) References Cited

U.S. PATENT DOCUMENTS

2010/0105132 A1* 4/2010 Totey .................. C12N 5/0663
435/352

FOREIGN PATENT DOCUMENTS

| CN | 103184190 A | 7/2013 |
| CN | 105062970 A | 11/2015 |
| CN | 105085938 A | 11/2015 |
| CN | 105087466 A | 11/2015 |
| CN | 105132369 A | 12/2015 |
| WO | WO-2006019357 A1 | 2/2006 |

OTHER PUBLICATIONS

Kim et al., Optimization of adipose tissue-derived mesenchymal stem cells by rapamycin in a murine model of acute graft-versus-host disease, p. 1-15. (Year: 2016).*
Corotchi et al., Testosterone stimulates proliferation and preserves stemness of human adult mesenchymal stem cells and endothelial progenitor cells, Rom J Morphol Embryol, 57(1): 75-80. (Year: 2016).*
Yang et al., Mechanism of Action of Icariin in Bone Marrow Mesenchymal Stem Cells, Stem Cells International, p. 1-12. (Year: 2019).*

* cited by examiner

*Primary Examiner* — Laura Schuberg
*Assistant Examiner* — Joseph Paul Miano
(74) *Attorney, Agent, or Firm* — Zhigang Ma

(57) ABSTRACT

A serum-free complete medium for inducing differentiation of a mesenchymal stem cell to a corneal epithelial cell in the field of differentiation induction of stem cells, prepared by the following method: uniformly mixing the serum-free complete medium, containing 5-10 μmol of resveratrol, 2-4 μmol of icariin, 1-3 nmol of aspirin, 1-3 nmol of parathyroid hormone, 5-10 nmol of hydrocortisone, 1-3 mg of rapamycin, 2-10 μg of testosterone, 2-10 μg of EPO, 2-10 μg of LIF and the balance of a corneal epithelial cell serum-free medium in per 1 L; and then performing sterilization by filtration. The disclosure uses resveratrol and icariin in combination with aspirin, parathyroid hormone, hydrocortisone, rapamycin, testosterone and growth factors to cooperatively induce directional differentiation, uses nontoxic induction components, is high in induction efficiency and short in induction time, and achieves high induced corneal epithelial cell activity, no cell transplantation rejection, no ethical problem and high safety.

2 Claims, 1 Drawing Sheet

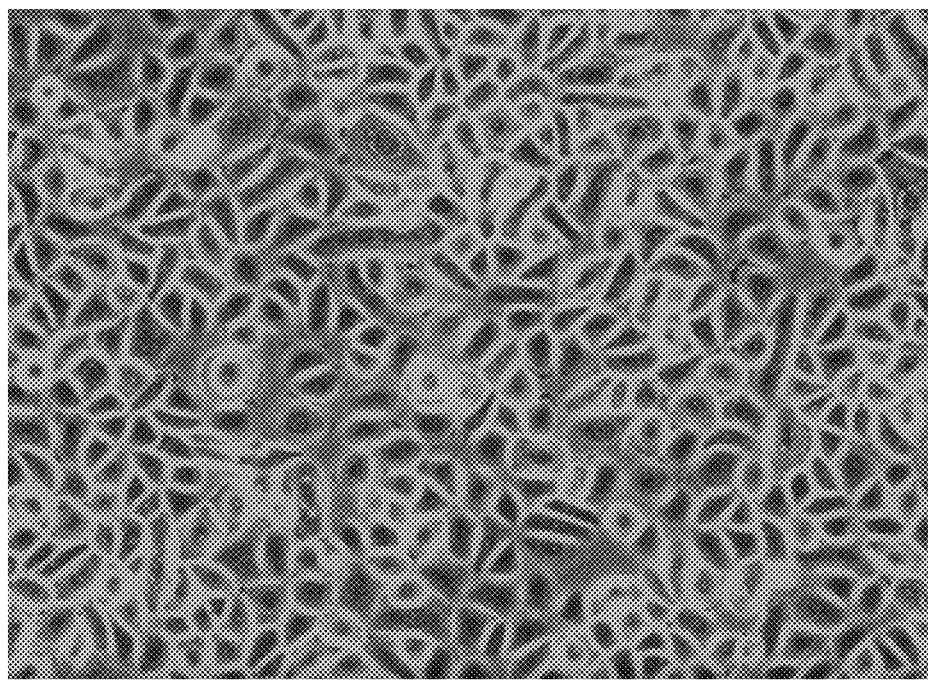

SERUM-FREE COMPLETE MEDIUM FOR INDUCING DIFFERENTIATION OF A MESENCHYMAL STEM CELL TO A CORNEAL EPITHELIAL CELL

TECHNICAL FIELD

The disclosure relates to the field of differentiation induction of stem cells, in particular to a serum-free complete medium for inducing differentiation of a mesenchymal stem cell to a corneal epithelial cell.

BACKGROUND

A corneal epithelial cell layer is located on an outer surface of a cornea. There are 5-6 layers of upper-layer cornea cells, each layer is arranged very orderly and tightly, and cells in a deepest layer are single-layer short columnar basal cells. There are 2-3 layers of polygonal wing cells on a deep layer, and uppermost layers are 2-3 layers of polygonal superficial cells. A shallowest layer of superficial cells are non-keratinized flat cells, gaps among the superficial cells are unclear, the superficial cells have smooth membranes, clear and transparent cytoplasm, and cytoplasm bulges mutually combined into bridges, and nuclei still exist. The corneal epithelial cell has extremely high light transmittance, strong resistance and strong regeneration ability, and even deep-layer cells can perform mitosis. The corneal epithelium can be generally recovered quickly after trauma and infection.

Limbal injury, limbal stem cell dysfunction, and epithelial cell loss can be caused by various pathogenic factors such as ocular trauma, surgical trauma, inflammation and drug toxicity, thus increasing the risk of corneal infection, perforation, and neovascularization. Corneal transplantation is the only effective means for curing corneal blindness at present. According to statistics, there are about 4 million to 5 million patients with corneal blindness in China, and most of them can regain the sight through corneal transplantation operations. However, only about ten thousand corneal transplantation operations can be performed in China every year for a main reason of seriously insufficient number of donated donor corneas, so that the popularization and application of the operations are limited, and most of patients with corneal blindness cannot regain the sight through corneal transplantation. Therefore, in-vitro reconstruction of tissue engineering corneas is an important breakthrough for solving the problem of insufficient donor cornea materials at present.

However, there are some bottleneck problems in the corneal tissue engineering at present, such as a source problem of corneal epithelial seed cells. Through the research about the corneal epithelium, people have a deeper understanding on the physiological and pathological characteristics of the cornea and corneal diseases, but a differentiated corneal epithelial cell has a very short in vitro growth life cycle and can only grow for 2-3 generations, so that the obtained cells are few in number and high in cost, and the research of corneal tissues and the construction of tissue engineering corneas are limited. Therefore, how to obtain corneal epithelial cells with a high proliferation ability and continuous division and growth ability to supplement continuous renewal of cells becomes a primary task for obtaining the corneal epithelial seed cells. By constructing a corneal epithelial cell line, cells required for different research purposes, such as epithelium proliferation and differentiation, testing of ophthalmic drugs, and development of novel treatment methods for corneal diseases can be stably provided for a long term.

Mesenchymal stem cells have wide sources, are easy to obtain and convenient for autotransplantation, have a strong proliferation ability, can always maintain their multidirectional differentiation potentials in an in vitro long-term culture process, can be differentiated into osteogenic cells, cartilage cells, tendon cells, muscle cells, adipose cells, nerve cells, liver cells, etc. under induction of specific conditions, and are ideal tissue engineering seed cells. The mesenchymal stem cells have become a hotspot of the research of stem cells, are induced to differentiate into corneal epithelial cells, and can be used for repairing corneal injury.

According to the differentiation of the stem cells, parts of genes are selectively activated or differentially expressed to control the cell phenotype and the specific distribution of proteins. Differentiation of the mesenchymal stem cell into a specific cell type mainly depends on gene activation, while various factor types and concentrations in an extracellular microenvironment are important factors for gene activation. A serum-free complete medium for inducing differentiation of a mesenchymal stem cell to a corneal epithelial cell of the disclosure uses traditional Chinese medicine components of resveratrol and icariin in combination with aspirin, parathyroid hormone, hydrocortisone, rapamycin, testosterone and growth factors to cooperatively induce the directional differentiation of the mesenchymal stem cell to the corneal epithelial cell, uses nontoxic induction components, is high in induction efficiency and short in induction time, and achieves high induced corneal epithelial cell activity, no cell transplantation rejection, no ethical problem and high safety.

SUMMARY

The disclosure is directed to provide a serum-free complete medium for inducing differentiation of a mesenchymal stem cell to a corneal epithelial cell with the advantages of high induction efficiency, few induction steps, short induction time, high induced corneal epithelial cell activity, no cell transplantation rejection, no ethical problem and high safety by aiming at defects of an existing induction culture and induction method.

For the above purpose, the disclosure adopts the following technical solution: the serum-free complete medium for inducing differentiation of a mesenchymal stem cell to a corneal epithelial cell is prepared by the following method: uniformly mixing the serum-free complete medium for differentiation induction, containing 5-10 μmol of resveratrol, 2-4 μmol of icariin, 1-3 nmol of aspirin, 1-3 nmol of parathyroid hormone, 5-10 nmol of hydrocortisone, 1-3 mg of rapamycin, 2-10 μg of testosterone, 2-10 μg of EPO, 2-10 μg of LIF and the balance of a corneal epithelial cell serum-free medium in per 1 L; and then performing sterilization by filtration.

Preferably, the serum-free complete medium for inducing differentiation of a mesenchymal stem cell to a corneal epithelial cell is prepared by the following method: uniformly mixing the serum-free complete medium for differentiation induction, containing 8 μmol of resveratrol, 3 μmol of icariin, 2 nmol of aspirin, 2 nmol of parathyroid hormone, 7 nmol of hydrocortisone, 2 mg of rapamycin, 7 μg of testosterone, 7 μg of EPO, 7 μg of LIF and the balance of a corneal epithelial cell serum-free medium in per 1 L; and then performing sterilization by filtration.

The serum-free complete medium for inducing differentiation of a mesenchymal stem cell to a corneal epithelial cell of the disclosure has the following advantages: 1, gene transfection is not needed, so that a gene modification and cancer risk is avoided; 2, induction steps are few; 3, the induction time is short; 4, the induction differentiation efficiency is high; 5, all inducer components of the disclosure are safe and nontoxic; and 6, after the differentiation induction of the mesenchymal stem cell to the corneal epithelial cell, no cell transplantation rejection and no ethical problem exist, the safety is high, and clinical application prospects are wide.

BRIEF DESCRIPTION OF THE DRAWINGS

The sole FIGURE shows morphology (×400) of corneal epithelial cells appeared after differentiation of mesenchymal stem cells induced by a medium of the disclosure.

DETAILED DESCRIPTION OF THE EMBODIMENTS

Experiment methods in the following examples are conventional methods unless otherwise specified. Instruments and reagents for the experiments are commercially available.

Example 1 All components of a serum-free complete medium for inducing differentiation of a mesenchymal stem cell to a corneal epithelial cell of the disclosure were commercially available: resveratrol, trademark: Sigma, and product code: R5010; icariin, trademark: Shanghai Weijing Biology, and product code: 489-32-7; aspirin, trademark: Sigma, and product code: A2093-100G; parathyroid hormone, trademark: Sigma, and product code: P7036; hydrocortisone, trademark: Sigma, and product code: H3160; rapamycin, trademark: TargetMol, and product code: T1537; testosterone, trademark: Sigma, and product code: T1500; EPO (hemopoietin), trademark: PeproTech, and product code: CYT-201; LIF (leukaemia inhibitory factor), trademark: PeproTech, and product code: 96-300-05-5; and corneal epithelial cell serum-free medium (CEpiCM), trademark: ScienCell, and product code: 6511.

A serum-free complete medium for inducing differentiation of a mesenchymal stem cell to a corneal epithelial cell was prepared from the following components respectively according to the following concentration proportion: per 1 L of the serum-free complete medium for differentiation induction contained 8 µmol of resveratrol, 3 µmol of icariin, 2 nmol of aspirin, 2 nmol of parathyroid hormone, 7 nmol of hydrocortisone, 2 mg of rapamycin, 7 µg of testosterone, 7 µg of EPO, 7 µg of LIF and the balance of a corneal epithelial cell serum-free medium. After being uniformly mixed, the components were sterilized by filtration.

Example 2 A serum-free complete medium for inducing differentiation of a mesenchymal stem cell to a corneal epithelial cell was prepared from the following components respectively according to the following concentration proportion: per 1 L of the serum-free complete medium for differentiation induction contained 5 µmol of resveratrol, 2 µmol of icariin, 1 nmol of aspirin, 1 nmol of parathyroid hormone, 5 nmol of hydrocortisone, 1 mg of rapamycin, 2 µg of testosterone, 2 µg of EPO, 2 µg of LIF and the balance of a corneal epithelial cell serum-free medium. After being uniformly mixed, the components were sterilized by filtration.

Example 3 A serum-free complete medium for inducing differentiation of a mesenchymal stem cell to a corneal epithelial cell was prepared from the following components respectively according to the following concentration proportion: per 1 L of the serum-free complete medium for differentiation induction contained 10 µmol of resveratrol, 4 µmol of icariin, 3 nmol of aspirin, 3 nmol of parathyroid hormone, 10 nmol of hydrocortisone, 3 mg of rapamycin, 10 µg of testosterone, 10 µg of EPO, 10 µg of LIF and the balance of a corneal epithelial cell serum-free medium. After being uniformly mixed, the components were sterilized by filtration.

Example 4 By taking human adipose-derived mesenchymal stem cells as an example, the induction medium prepared in Example 1 was used for performing a corneal epithelial cell differentiation induction experiment on the mesenchymal stem cells. The steps were as follows:

Adipose-derived mesenchymal stem cells were induced to differentiate into corneal epithelial cells: $3^{rd}$-generation MSC was inoculated into a 6-hole cell culture plate previously loaded with polylysine-treated sterile cover glasses to prepare round coverslips. Differentiation induction was performed when the cells were fused to about 80% and grew vigorously. Experiment groups are shown in table 1:

TABLE 1

Experiment groups

| Groups | Induction conditions |
| --- | --- |
| Induction group of the disclosure | Induction for 5 d by the induction medium of the disclosure. |
| Conditioned medium group | Preparation of a conditioned medium: human limbal stem cells were cultured by a DMEM/F12 medium containing 20% FBS + 10 µg/L EGF in a 37° C. 5% $CO_2$ incubator. The medium was changed once every 2 d. The medium changed in each time was collected and transferred into a centrifuge tube to be centrifugated at 1000 rpm/min for 5 min. Supernatants were collected in a sterile tube to be put into a −20° C. refrigerator for use. Induction was performed for 30 d by using the above conditioned medium. |
| Co-culture group | According to instructions of Millipore Company, a Transwell co-culture system was used. The human limbal stem cells were inoculated into Transwell chambers and were then put into the 6-hole cell culture plate for co-culture and induction for 7 d together with the mesenchymal stem cell. |

After induction, the cells were identified. CK3, CK12 and CK19 were selected to be used as corneal epithelial cell markers. Expression conditions of CK3, CK12 and CK19 before and after the induction were detected by an immunocytochemical method. 4 cover glasses were randomly extracted, 5 sights were randomly selected in a 200-time field, and the proportion of positive cells was respectively calculated. The proportion of the positive cells in total cells was expressed by mean±standard deviation ($\bar{x}\pm s$). Statistical analysis was performed by SPSS11.0 software. Experiment data was expressed by ($\bar{x}\pm s$). Variance analysis was adopted for comparison among a plurality of groups. $x^2$ inspection was adopted for rate comparison between two groups. $P<0.05$ showed existence of statistical significance. Induction results of the three groups are as shown in Table 2:

TABLE 2

Induction results of three groups (n = 20, x̄ ± s)

| Groups | Immunocytochemical method | | |
|---|---|---|---|
| | CK3 | CK12 | CK19 |
| Induction group of the disclosure | (92.4 ± 1.3)% | (89.5 ± 1.6)% | (93.7 ± 1.1)% |
| Conditioned culture group | (32.5 ± 0.9)% | (29.6 ± 0.8)% | (24.4 ± 0.5)% |
| Co-culture group | (41.6 ± 1.5)% | (37.5 ± 2.0)% | (44.2 ± 1.7)% |

As shown in Table 2, the positive cell ratio of CK3, CK12 and CK19 after the differentiation induction of the induction group of the disclosure was higher than that of the conditioned medium group and that of the co-culture group (P<0.05). It showed that the induction efficiency of the medium of the disclosure was obviously higher than that of the conditioned culture group and that of the co-culture group, and reached 90% or higher.

Based on the above, the serum-free complete medium for inducing differentiation of a mesenchymal stem cell to a corneal epithelial cell of the disclosure has a highest induction efficiency and shortest induction time, and is worthy of popularization.

What is claimed is:

1. A serum-free complete medium for inducing differentiation of a mesenchymal stem cell to a corneal epithelial cell, prepared by the following method: uniformly mixing the serum-free complete medium for differentiation induction, containing 5-10 μmol of resveratrol, 2-4 μmol of icariin, 1-3 nmol of acetylsalicylic acid, 1-3 nmol of parathyroid hormone, 5-10 nmol of hydrocortisone, 1-3 mg of rapamycin, 2-10 μg of testosterone, 2-10 μg of erythropoietin (EPO), 2-10 μg of leukemia inhibitory factor (LIF) and the balance of a corneal epithelial cell serum-free medium in per 1 L; and then performing sterilization by filtration.

2. A serum-free complete medium for inducing differentiation of a mesenchymal stem cell to a corneal epithelial cell, prepared by the following method: uniformly mixing the serum-free complete medium for differentiation induction, containing 8 μmol of resveratrol, 3 μmol of icariin, 2 nmol of acetylsalicylic acid, 2 nmol of parathyroid hormone, 7 nmol of hydrocortisone, 2 mg of rapamycin, 7 μg of testosterone, 7 μg of erythropoietin (EPO), 7 μg of leukemia inhibitory factor (LIF) and the balance of a corneal epithelial cell serum-free medium in per 1 L; and then performing sterilization by filtration.

* * * * *